US008034805B2

(12) United States Patent
Hradil et al.

(10) Patent No.: US 8,034,805 B2
(45) Date of Patent: Oct. 11, 2011

(54) METHODS FOR THE PREPARATION OF SALTS OF 2-[2-(4-DIBENZO[B,F][1,4] THIAZEPIN-11-YL-1-PIPERAZINYL) ETHOXYL]ETHANOL (QUETIAPINE) AND FOR THE PURIFICATION THEREOF

(75) Inventors: Pavel Hradil, Hlusovice (CZ); Lubomir Kvapil, Slatinice (CZ); Roman Gabriel, Olomouc (CZ); Martin Grepl, Hlusovice (CZ); Jan Novotny, Olomouc (CZ); Petr Slezar, Olomouc (CZ); Radek Melnicky, Sternberk (CZ)

(73) Assignee: Farmak, A.S., Olomouc (CZ)

( * ) Notice: Subject to any disclaimer, the term of this patent is extended or adjusted under 35 U.S.C. 154(b) by 347 days.

(21) Appl. No.: 12/306,691

(22) PCT Filed: Aug. 31, 2006

(86) PCT No.: PCT/CZ2006/000054
§ 371 (c)(1),
(2), (4) Date: Dec. 25, 2008

(87) PCT Pub. No.: WO2008/003270
PCT Pub. Date: Jan. 10, 2008

(65) Prior Publication Data
US 2009/0275747 A1 Nov. 5, 2009

(30) Foreign Application Priority Data
Jul. 3, 2006 (CZ) .................. PV 2006-434

(51) Int. Cl.
*A61K 31/554* (2006.01)
*C07D 281/16* (2006.01)

(52) U.S. Cl. .................. 514/211.13; 540/551

(58) Field of Classification Search ............ 514/211.13; 540/551
See application file for complete search history.

(56) References Cited

U.S. PATENT DOCUMENTS

| 6,372,734 B1 | 4/2002 | Snape |
| 2004/0220400 A1 | 11/2004 | Diller |
| 2004/0242562 A1 | 12/2004 | Parthasaradhi et al. |
| 2006/0063927 A1 | 3/2006 | Etlin et al. |

FOREIGN PATENT DOCUMENTS

| EP | 0 240 228 | 10/1987 |
| WO | WO 03/080065 | 10/2003 |
| WO | WO 2004/078735 | 9/2004 |
| WO | WO 2006/027789 | 3/2006 |
| WO | WO 2006/135544 | 12/2006 |

OTHER PUBLICATIONS

International Search Report for International Application No. PCT/CZ2006/000054 mailed Jun. 1, 2007.

*Primary Examiner* — Brenda Coleman
(74) *Attorney, Agent, or Firm* — Pearl Cohen Zedek Latzer, LLP

(57) ABSTRACT

A method for the preparation of salts of 2-[2-(4-dibenzo[b,f] [1,4]thiazepin-11-yl-1 -piperazinyl)ethoxy]ethanol (quetiapine) from the quetiapine base and the respective acid, wherein the salt is precipitated from a mixture of solvents, the mixture being either a mixture of an aromatic hydrocarbon and a ketone or ester, or that of an aromatic hydrocarbon, water and a ketone or ester. The salts of quetiapine are purified by partial crystallization, wherein only a part of the salt of quetiapine is dissolved in a $C_1$ to $C_6$ alcohol used.

8 Claims, No Drawings

METHODS FOR THE PREPARATION OF SALTS OF 2-[2-(4-DIBENZO[B,F][1,4] THIAZEPIN-11-YL-1-PIPERAZINYL) ETHOXYL]ETHANOL (QUETIAPINE) AND FOR THE PURIFICATION THEREOF

CROSS-REFERENCE TO RELATED APPLICATIONS

This application is a National Phase Application of PCT International Application No. PCT/CZ2006/000054, entitled "METHODS FOR THE PREPARATION OF SALTS OF 2-[2-(4-DIBENZO [B,F][1,4]THIAZEPIN-11-YL-1-PIPERAZINYL)ETHOXYL]ETHANOL (QUETIAPINE) AND FOR THE PURIFICATION THEREOF", International Filing Date Aug. 31, 2006, published on Jan. 10, 2008 as International Publication No. WO 2008/003270, which in turn claims priority from Czechoslovakian Patent Application No. PV 2006-434, filed Jul. 3, 2006, both of which are incorporated herein by reference in their entirety.

TECHNICAL FIELD

The invention concerns a new method of preparation of salts of 2-[2-(4-dibenzo[b,f][1,4]thiazepin-11-yl-1piperazinyl)ethoxy]ethanol (quetiapine) and their purification, especially preparation and purification of quetiapine hemifumarate with polymorphy, designated polymorphous structure I in the literature, which is used as an antipsychotic, for example for the treatment of schizophrenia, depressions, and the like.

BACKGROUND ART

Several different methods of preparation of salts of 2-[2-(4-dibenzo[b,f][1,4]thiazepin-11-yl-1-piperazinyl)ethoxy]ethanol (quetiapine) and their purification, e.g. of quetiapine hemifumarate in various crystalline modifications, have been described so far.

In the original patent EP 0 240 228, quetiapine hemifumarate is prepared from the quetiapine base, which has been previously purified by column chromatography. Thus purified base is mixed hot with fumaric acid in ethanol, giving a solution from which, after cooling, quetiapine hemifumarate is crystallized.

A similar method of preparation is described in patent application US 2006/0063927.

In another patent, U.S. Pat. No. 6,372,734, quetiapine hemifumarate is prepared from the crystallized quetiapine base, which is, under boiling, mixed with a solution of fumaric acid in a mixture ethanol/methanol. Crystallized quetiapine hemifumarate is isolated after being cooled to 0° C.

In US Pat. Appl. Publ. 2004/0220400, quetiapine hemifumarate is prepared by adding fumaric acid, after completion of the reaction, directly to the reaction solution which contains toluene, n-butanol, or dimethylformamide as the solvent. After isolation, crude quetiapine hemifumarate has to be purified by further crystallizations from alcohols. The yields range about 70% of the theory.

In US Pat. Appl. Publ. 2004/0242562, the purified quetiapine base is dissolved in a solvent selected from the group of ketones, esters, or ethers. Fumaric acid is then added, and after it dissolves, quetiapine hemifumarate is allowed to crystallize. The yields are about 85%. The product obtained is further purified by crystallizations.

According to international patent application WO 2004/078735, quetiapine base is dissolved in a solvent selected from the group of ketones or esters of formic or acetic acids. Fumaric acid is then added, and after it dissolves, quetiapine hemifumarate is allowed to crystallize.

International patent application WO 03/080065 describes, inter alia, purification of quetiapine hemifumarate by dissolving quetiapine hemifumarate in a mixture containing water, a lower alcohol, or a dipolar aprotic solvent. After it dissolves, it is allowed to crystallize spontaneously, or is precipitated with a suitable solvent.

According to international patent application WO 2006/027789, quetiapine hemifumarate is prepared by dissolving the quetiapine base in acetone and by subsequent action of fumaric acid.

Disadvantages of the aforementioned methods:

In most cases, pure quetiapine base (for example in the crystalline form) is used as the starting substance, which has to be isolated first and then dissolved again.

The obtaining of pure quetiapine base is demanding for energy and time, involving losses thereof and thermal exposition during concentrating the solutions, which leads to formation of impurities.

Another common disadvantage comprises the relatively high solubility of salts of quetiapine in the solvents in which crystallization proceeds, and losses during crystallization associated.

To eliminate the aforementioned disadvantages, the authors of this invention have carried out extensive research with the following result. Numerous dependencies, unknown up to date, have been discovered during the preparation and purification of salts of quetiapine. It has been found out that the quetiapine base does not have to be purified either from side substances, or from residual solvents or water. The method according to the invention makes it possible to combine several steps and process the product without further isolating, drying, or purifying. Therefore, this method has a significant influence on the yields, the rate of processing, technological equipment, and hence also costs.

It has been found out that in forming the salt in a mixture of an aromatic hydrocarbon with ketones or esters in a suitable ratio the drawbacks of the methods in which these solvents are used separately are removed, namely toluene in case of US Pat. Appl Publ. 2004/0220400, and ketones or esters in US Pat. Appl. Publ. 2004/0242562. In the case of aromatic hydrocarbons, a sticky, difficult-to-isolate product is formed, and in the case of ketones or esters, it is necessary to remove the extraction solvent (mostly toluene), to isolate pure quetiapine base, and the yield of the formation of the salt is lower.

DISCLOSURE OF INVENTION

The invention discloses a method of preparation of salts of 2-[2-(4-dibenzo[b,f][1,4]thiazepin-11-yl-1-piperazinyl) ethoxy]ethanol (quetiapine) from the quetiapine base and the respective acid, which consists in precipitating the salt from a mixture of solvents, which is either a mixture of an aromatic hydrocarbon and a ketone or ester, or that of an aromatic hydrocarbon, water and a ketone or ester.

A preferable embodiment of the method of preparing the salts includes use of toluene and acetone or methylethylketone as the mixture of solvents.

Another preferable embodiment of the method of preparing the salts includes use of toluene and ethyl acetate as the mixture of solvents.

The amount of the aromatic hydrocarbon in the reaction mixture can be up to 80% by volume.

The amount of water in the reaction mixture can be up to 5% by volume.

Although fumaric acid is insoluble in either toluene or acetone, the addition of the solution of quetiapine base in an aromatic hydrocarbon to the suspension of the acid in a ketone or ester results first in formation of a solution and then in precipitation of a crystalline product. Only with an amount of the aromatic hydrocarbon higher than 80% a two-phase reaction mixture is formed and a sticky, not properly crystalline salt precipitates. In the proposed method, even the presence of a certain amount of water in the reaction mixture causes no problems; it is therefore possible to use the wet base or solvents, which brings about many advantages, particularly from the industrial point of view.

In this case, an easily filtrable substance precipitates in practically quantitative yield. Other advantages include simplicity of the method, as it is not necessary to distil off toluene, used for the extraction, to dryness, and formation of a pure product because impurities are easily removed during filtration with activated carbon.

It has been further found out that if the purification is carried out in the manner where the amount of alcohol does not suffice to dissolve the salts of quetiapine, and a crystalline phase is permanently present in the reaction mixture, the purification effect is the same as in the case of crystallization, but the losses of the product are, in an optimal case, only 3% as opposed to 10 to 15% even for crystallization being carried out as carefully as possible; also, the consumption of solvents and the time needed for the operation are several times lower. Moreover, it is possible to obtain in this manner a uniform, easily filtrable crystal that can be used for the preparation of dosage forms after common sifting, instead of significantly more expensive grinding.

Another aspect of the invention discloses purification of salts of 2-[2-(4-dibenzo[b,f][1,4]-thiazepin-11-yl-1-piperazinyl)ethoxy]ethanol (quetiapine), which consists in purifying the salts by partial crystallization, wherein only a part of the salt of quetiapine is dissolved in a $C_1$ to $C_6$ alcohol used.

A preferable embodiment includes use of methanol for the partial crystallization.

Advantages of the proposed method of preparation of salts of quetiapine and their purification according to the present invention are as follows:

Quetiapine base is not isolated from the reaction mixture and it need not be purified;
a significant increase of the yield;
shorter reaction times compared to prior methods;
lower consumption of solvents;
lower losses during crystallization.

EXAMPLES

The essence of the methods according to the invention is further demonstrated in the following examples. These examples have an illustrative character and do not limit the extent of the invention in any case.

Example 1

Preparation of Quetiapine Hemifumarate

A suspension of 1.62 g (0.014 mol) of fumaric acid in 100 ml of acetone is brought to the boil. 100 ml of a toluene solution containing 10.77 g (0.028 mol) of pure quetiapine base is added to the boiling suspension, and the reaction mixture is heated to the boil for another 5 minutes. The precipitated crystalline product is cooled to approximately 20° C., and the reaction mixture is stirred for another 60 minutes. The precipitated crystalline quetiapine hemifumarate is filtered, washed, and dried.

The yield is 12.28 g (0.028 mol), i.e. 99% of the theory, having the HPLC purity 99.86%, and melting point 175.8° C.

Example 2

Preparation of Quetiapine Hemifumarate

A suspension of 1.62 g (0.014 mol) of fumaric acid in 100 ml of ethyl acetate is brought to the boil. At this temperature, 100 ml of a toluene solution containing 10.77 g (0.028 mol) of pure quetiapine base is added, and the reaction mixture is allowed to boil for about 5 minutes. During this period a crystalline product starts to precipitate, which is then cooled to ca. 20° C. and is stirred at this temperature for 60 minutes. After being sucked off and dried, approximately 12.28 g (0.028 mol) of quetiapine hemifumarate is obtained, i.e. 99% of the theory, having the HPLC purity 99.76%, and melting point 175.7° C.

Example 3

Preparation of Quetiapine Hemifumarate 0.8 g (0.007 mol) of fumaric acid is suspended in a solution of 30 ml of acetone and 0.3 ml of water. The suspension is brought to the boil, and 30 ml of a toluene solution containing 5.38 g (0.014 mol) of pure quetiapine base is added. The solution is refluxed for approximately 5 minutes, then cooled to a temperature of 0 to 5° C. and stirred at this temperature for 60 minutes. After being sucked off and dried, 5.7 g (0.013 mol) of quetiapine hemifumarate is obtained, i.e. 99.6% of the theory, having the HPLC purity 99.87%, and melting point 175.9° C.

Example 4

Preparation of Quetiapine Hemifumarate 0.65 g (0.006 mol) of fumaric acid is suspended in a solution of 25 ml of acetone and 5 ml of water, the solution is brought to the boil, and 25 ml of a toluene solution containing 4.5 g (0.012 mol) of pure quetiapine base is added. The solution is refluxed for approximately 5 minutes and then cooled to a temperature of 0 to 5° C., at which crystals start to precipitate. It is stirred at this temperature for 90 minutes. After being sucked off and dried, 3.8 g (0.009 mol) of quetiapine hemifumarate is obtained, i.e. 64.5% of the theory, having the HPLC purity 99.82%, and melting point 172° C.

Example 5

Preparation of Quetiapine Oxalate

A suspension of 11.5 g (0.091 mol) of oxalic acid in 40 ml of acetone is brought to the boil. A solution of 31.8 g (0.083 mol) of quetiapine base in 290 ml of acetone and 10 ml of toluene is added to the suspension. The resulting solution is heated to the boil for 5 minutes, and the reaction mixture is then cooled to 30 to 25° C., at which temperature it is stirred for 1 hour. After this period, the crystals are filtered off and dried in a hot-air drier at 50° C. for 2 hours.

The yield: 34.5 g (0.073 mol) of quetiapine oxalate, i.e. 89% of the theory, having the, HPLC purity 99.59%, and melting point 150.5° C.

Example 6

Purification of Quetiapine Hemifumarate by Partial Crystallization 8 g (0.0181 mol) of quetiapine hemifumarate is suspended in 40 ml of methanol, the suspension is stirred under reflux for 10 minutes, cooled gradually to 0 to 5° C. and stirred at this temperature for another 30 minutes. The crystals are filtered off, washed with 20 ml of acetone, and dried in a hot-air drier at 60° C. for 45 minutes.

The yield: 7.7 g (0.0174 mol) of crystalline quetiapine hemifumarate, i.e. 96.3% of the theory, having the HPLC purity 99.92%, and melting point 176.0° C.

Example 7

Purification of Quetiapine Hemifumarate by Partial Crystallization 8 g (0.0181 mol) of quetiapine hemifumarate is suspended in 45 ml of ethanol, the suspension is brought to the boil and stirred under reflux for 10 minutes. Then it is cooled gradually to 0 to 5° C. and stirred at this temperature for 30 minutes. After this period, the crystals are filtered off, washed with 20 ml of acetone, and dried in a hot-air drier at 60° C. for 45 minutes.

The yield: 7.8 g (0.0177 mol) of crystalline quetiapine hemifumarate, i.e. 97.5% of the theory, having the HPLC purity 99.85%, and melting point 175.5° C.

Example 8

Purification of Quetiapine Hemifumarate by Partial Crystallization 1 g (0.0023 mol) of quetiapine hemifumarate is suspended in 5 ml of isopropyl alcohol. The mixture is stirred at 22° C. for 15 minutes, then it is filtered by suction, washed with 5 ml of acetone, and dried in a hot-air drier at 80° C.

The yield: 0.95 g (0.0022 mol) of crystalline quetiapine hemifumarate, i.e. 95% of the theory, having the HPLC purity 99.75%, and melting point 175.1° C.

Example 9

Preparation of Quetiapine Hemifumarate

A suspension of 1.2 g (0.0103 mol) of fumaric acid in 10 ml of acetone is brought to the boil. 40 ml of a toluene solution containing 7.53 g (0.0196 mol) of pure quetiapine base is added to the boiling suspension. An oily suspension is formed, which crystallizes under boil during 3 to 4 minutes. Reflux is maintained for 5 minutes and then the suspension is cooled to 20° C. and stirred for 60 minutes. Precipitated crystalline quetiapine hemifumarate is isolated by filtration and dried.

Yield: 4.6 g (0.0104 mol) of crystalline quetiapine hemifumarate, i.e. 53.2% of the theory, having the HPLC purity 99.6%, and melting point 175.1° C.

Example 10

Preparation of Quetiapine Hemifumarate

A suspension of 0.8 g (0.007 mol) of fumaric acid in 120 ml of acetone is brought to the boil. 30 ml of a toluene solution containing 5.06 g (0.0132 mol) of pure quetiapine base is added to the boiling suspension and the reaction mixture is stirred under boil for another 5 minutes. The precipitated crystalline product is cooled to approximately 20° C. and stirred for another 60 minutes. Precipitated crystalline quetiapine hemifumarate is isolated by filtration, washed and dried.

Yield: 5.77 g (0.0131 mol) of crystalline quetiapine hemifumarate, i.e. 99.0% of the theory, having the HPLC purity 99.85%, and melting point 175.7° C.

INDUSTRIAL APPLICABILITY

The method of preparation of salts of quetiapine and their purification according to the invention can be carried out under advantageous technical and economical conditions, while retaining a sufficiently high yield and high purity.

The invention claimed is:

1. A method for the preparation of salts of 2-[2-(4-dibenzo[b,f][1,4]thiazepin-11-yl-1-piperazinyl)ethoxy]ethanol (quetiapine) from the quetiapine base and the respective acid, wherein the reaction is carried out in a mixture of solvents, the mixture being either a mixture of an aromatic hydrocarbon and a ketone or ester, or that of an aromatic hydrocarbon, water and a ketone or ester.

2. The method according to claim 1, wherein the mixture of solvents consists of toluene and acetone or methylketone.

3. The according to claim 1, wherein the mixture of solvents consists of toluene and ethyl acetate.

4. The method according to claim 1, wherein the amount of the aromatic hydrocarbon in the reaction mixture is up to 80% by volume.

5. The method according to claim 1, wherein the amount of water in the reaction mixture is up to 5% by volume.

6. The method according to claim 1, wherein the volume ratio of the aromatic hydrocarbon to the other solvent is 1:1.

7. A method for the purification of salts of 2-[2-(4-dibenzo[b,f][1,4]thiazepin-11-yl-1-piperazinyl)ethoxy]ethanol (quetiapine), wherein the salt is subjected to partial crystallization in a $C_1$ to $C_6$ alcohol, such that only a part of the salt dissolves in said alcohol.

8. The method according to claim 7, wherein methanol is used for the partial crystallization.

* * * * *

UNITED STATES PATENT AND TRADEMARK OFFICE
CERTIFICATE OF CORRECTION

| | | |
|---|---|---|
| PATENT NO. | : 8,034,805 B2 | Page 1 of 1 |
| APPLICATION NO. | : 12/306691 | |
| DATED | : October 11, 2011 | |
| INVENTOR(S) | : Pavel Hradil et al. | |

It is certified that error appears in the above-identified patent and that said Letters Patent is hereby corrected as shown below:

Col. 6, lines 33-34

Claim 3 should read:

3. The method according to claim 1, wherein the mixture of solvents consists of toluene and ethyl acetate.

Signed and Sealed this
Tenth Day of January, 2012

David J. Kappos
*Director of the United States Patent and Trademark Office*